United States Patent [19]
Ostashko et al.

[11] 4,039,934
[45] Aug. 2, 1977

[54] METHOD OF AND APPARATUS FOR MEASURING IONIC ELECTRIC CONDUCTANCE OF OBJECTS

[76] Inventors: Fedor Ivanovich Ostashko, p/o Kulinichi, o/kh"Ukrainka" ulitsa Olkhovskaya, 5, kv. 6; Igor Nikolaevich Mirny, p/o Kulinichi, o/kh"Ukrainka" ulitsa Olkhovskaya, 13, kv. 15, both of Kharkov, U.S.S.R.

[21] Appl. No.: 422,922

[22] Filed: Dec. 7, 1973

[51] Int. Cl.$^2$ .......................................... G01N 27/42
[52] U.S. Cl. ................................................. 324/30 R
[58] Field of Search ..................... 324/30 R, 30 B, 111

[56] References Cited

U.S. PATENT DOCUMENTS

| 2,468,687 | 4/1949 | Schmitt | 324/111 X |
| 2,560,857 | 7/1951 | Gambetta | 324/30 |
| 2,651,751 | 9/1953 | Heath | 324/30 |
| 3,879,657 | 12/1973 | Nystuen et al. | 324/30 R |

FOREIGN PATENT DOCUMENTS

| 1,233,958 | 2/1967 | Germany | 324/30 |

OTHER PUBLICATIONS

Johnson et al., "Bipolar Pulse Technique . . . " Analytical Chemistry vol. 42, No. 3, Mar. 1970, pp. 329-335.
Kotter, F. R., "Instrumentation for . . . " The Review of Scientific Instruments, vol. 28, No. 3, Mar. 1967, pp. 178-181.

*Primary Examiner*—John K. Corbin
*Assistant Examiner*—Rolf Hille
*Attorney, Agent, or Firm*—J. Harold Nisse

[57] ABSTRACT

The method of the invention is mainly intended for studying biological objects, and in particular cervical secretion of cows for the purposes of the pregnancy diagnosis. The method comprises the step of passing through the object being tested of such a short-term current pulse that the total amount of electricity passed through the object during the measurement should not exceed $1.35 \cdot 10^{-3}$C, with a permissible error of the measurement being ±2.5%. The apparatus comprises a current pulse relaxation generator, measuring electrodes and a capacitor which memorizes the current passed through the object being tested and is coupled to a current indicator.

5 Claims, 3 Drawing Figures

METHOD OF AND APPARATUS FOR MEASURING IONIC ELECTRIC CONDUCTANCE OF OBJECTS

The present invention relates to equipment for measuring electric conductance, and more specifically to a method of and apparatus for measuring ionic electric conductance of biological objects.

Prior art apparatus intended for similar purposes mainly comprise a power supply source, measuring electrodes coupled thereto and positioned adjacent the zone of a tested object to be measured, and a current meter.

In modern biological researches the method of measuring electric conductance is being widely used in studying the properties of living organisms, since the value of the electric conductance allows the evaluation of physical and chemical properties, structure and functional activity of biological objects.

The reliability of the data obtained in such studies depends to a considerable extent upon the accuracy of measurement of the actual electric conductance value.

There are methods and apparatus offering a possibility of measuring the electric conductance to DC with high accuracy, but they can be successfully used only for objects exhibiting the electronic conductivity. The electric conductance of such objects is determined by the transfer of electric charges with electrons, and hence it does not depend either upon the presence of current, or upon its magnitude.

Normally biological objects and solutions contain an electrolytic phase; their electric conductance is determined by the presence of ions and is accompanied by electrolysis, polarization of the current-leading electrodes, heating of the object being tested, as well as by changes in its chemical composition. The above-mentioned phenomena result in errors in the measurements of the ionic conductance. This is due to the following reasons.

Error due to polarization of the current-leading (measuring) electrodes. The coupling of an object to a measuring apparatus is effected by means of current-leading electrodes. The introduction of the electrodes into the object results in the appearance of polarization EMF at the electrode-liquid phase boundary. During the passage of electric current through the object in the course of measurement the counter-EMF of polarization will reduce the actual conductance of the object.

Error due to heating of the object. Joule heat, which is developed in the object during the passage of electric current therethrough, will result in a temperature growth in the zone of location of the electrodes. This will result in an increased mobility of ions, and thereby in apparent increase in the electric conductance.

Error due to electrolysis. The passage of electric current through the object is accompanied by electrolysis. Gaseous products of electrolysis appear in the form of non-conductive bubbles between the measuring electrodes, thereby hampering ions movement. In this case apparent reduction of the actual electric conductance will be observed.

Error due to changes in chemical composition of the object. Since during the electrolysis chemical composition of the object is changed, this will result in a change of the initial concentration of active ions. Therefore, apparent change in the actual electric conductance will occur. Thus, the use of the exsisting methods and apparatus for measuring electric conductance of biological objects and solutions results in the appearance of errors substantially reducing the possibilities offered by the electrometric method of investigation.

In view of the above-said, it is an object of the present invention to eliminate the above disadvantages of prior art methods of and apparatus for measuring electric conductance of biological objects.

Therefore, it is an object of the invention to provide a method of measuring ionic conductance of objects which eliminates the danger of the influence of heating of the tested object by current passing therethrough as well as the influence of electrolysis in the medium being tested and changes in chemical composition of the object at the instant of measurement on the accuracy of the measurement.

It is another object of the invention to provide an apparatus for measuring ionic conductance which eliminates the error due to polarization of the measuring electrodes during the measurement and ensures high accuracy of the data obtained on the basis of electric conductance of biological objects.

Still another object of the invention is to provide a method of and apparatus for measuring ionic conductance, which feature a simple circuitry, high functional reliability and speed.

An object of the invention is also to provide a method of and apparatus for measuring electric conductance for the purpose of diagnosis of physiological state of the sexual sphere in cows both under the laboratory and field conditions.

With these and other objects in view the invention consists in the provision of a method of and an apparatus for measuring ionic electric conductance of objects, wherein the pattern of application and collection of a measuring pulse is modified, thereby eliminating the appearance of errors introduced into the result obtained by the process of measurement proper.

The above objects are accomplished by the provision of a method for measuring ionic electric conductance of preferably biological objects by establishing a current flow in a predetermined zone of the tested object, which, according to the invention comprises the passage in the course of the measurement through a predetermined zone of the tested object of a current of such magnitude and during such a relatively short time interval that a total amount of electricity passing through the tested object during the time of measurement should not exceed about $1.35 \cdot 10^{-3}$ coulomb, with the corresonding permissible error of the measurement being $\pm 2.5\%$.

It is for the above-mentioned permissible error of the measurement of $\pm 2.5\%$, that the selected releatively short term and minimum pulse of electric power makes it possible to avoid the adverse effect on the tested biological object during the measurement and does not permit the errors to appear.

In one of the embodiments of the present invention there is provided the passage of electric current for a time not exceeding 0.25 sec during the measurement of ionic electric conductance of cervical secretion of a cow for the purposes of pregnancy diagnosis, where the current is passed through the sampled secretion.

According to the invention the process of passing electric current through the object being tested and the process of evaluating the current, which has been passed through, are preferably time-shared so that electric current is first passed through the object during a short time interval, and then the value of the current, which has been passed through, is memorized and evaluated.

An apparatus for carrying out the above-described method of measuring ionic electric conductance of objects comprises a power supply source, measuring electrodes coupled thereto and adapted to be positioned adjacent the zone of measurement of the object being tested, and a current meter, the apparatus according to the invention being furthermore provided with means for application of a short-term current pulse and means for memorizing the value of the current passed though the object, which is proportional to the value of electric conductance of the object.

According to one of the embodiments of the apparatus of this invention, it comprises means for short-circuiting the measuring electrodes after the measuring step so as to remove electrochemical potential from the electrodes surface.

This means is required for eliminating an error in reproducing the measuring steps as it will become more apparent from the description herebelow.

Means for application of a short-term current pulse to the electrodes preferably comprises a relaxation current-pulse generator.

In one of the embodiments of the invention means for memorizing the current value may comprise an electrolytic capacitor which is charged from the measuring electrode circuit via a diode at a voltage proportional to the electric conductance of the object, and in addition the apparatus preferably comprises switching means for coupling said capacitor to the current meter for measuring current using a comparison circuit.

The invention will now be described in detail with reference to the accompanying drawings, in which.

Figure 1:
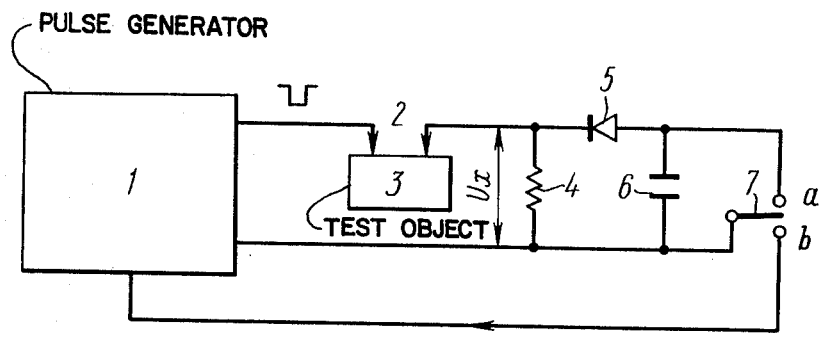
FIG. 1 shows an embodiment of the functional diagram of the apparatus for measuring ionic electric conductance.

In selecting the methods of reducing the errors of measurements of electric conductance of biological objects the operation and design considerations, as well as specific conditions and purposes of the application of the method are of a great importance.

In particular, it was contemplated to use the method of measuring electric conductance in diagnostics of the physiological state of the sexual sphere in cows. The method of diagnosis is based upon the existence of a correlation relationship between the value of electric conductance of cervical secretion in cows (cervix mucus) and the ovary function in these animals. It was found that during the pregnancy cervical secretion exhibits low electric conductance, while being of a high value during sexual heat. This phenomenon allows reliable determination of pregnancy as early as 21 days after the fecundation, which is not possible with any other of the existing methods. Furthermore, the value of electric conductance of cervical secretion at the stage of sexual excitement of the animal may be useful for prediction of the moment of the ovulation so as to procede with artificial insemination of a dam at the time most favourable for conception.

Therefore, in order to apply the electrometric method of pregnancy diagnosis and to determine optimum time for insemination, it is necessary to have an apparatus ensuring the measurement of electric conductance of cervical secretion with sufficient accuracy and at the stock-keeping locations. The latter condition imposes additional requirements for the equipment as to its simplicity and portability.

The electric conductance of secretion must be measured at the stock-keeping locations due to the fact that the products of vital activity of microscopic flora of the secretion have a misleading effect, these products changing the electrolytic composition of the object of measurement during its long-term storage.

Since cervical secretion normally contains non-conductive air bubbles, it is necessary to have sufficiently convenient visual field in the contact zone so as to select the most uniform zone of the object free of extraneous occlusions.

Thus, the method of measuring electric conductance of cervical secretion must ensure high accuracy (error less) value of electric conductance of cervical secretion at the stage of sexual excitement of the animal may be useful for prediction of the moment of the ovulation so as to procede with artificial insemination of a dam at the time most favourable for conception.

Therefore, in order to apply the electrometric method of pregnancy diagnosis and to determine optimum time for insemination, it is necessary to have an apparatus ensuring the measurement of electric conductance of cervical secretion with sufficient accuracy and at the stock-keeping locations. The latter condition imposes additional requirements for the equipment as to it simplicity and portability.

The electric conductance of secretion must be measured at the stock-keeping locations due to the fact that the products of vital activity of microscopic flora of the secretion have a misleading effect, these products changing the electrolytic composition of the object of measurement during its long-term storage.

Since cervical secretion normally contains non-conductive air bubbles, it is necessary to have sufficiently convenient visual field in the contact zone so as to select the most uniform zone of the object free of extraneous occlusions.

Thus, the method of measuring electric conductance of cervical secretion must ensure high accuracy (error less) than $\pm 2.5\%$). The apparatus for carrying out the method must be of a small size, portable, with low power consumption, while reliably operating at elevated humidity and within a wide range of ambient temperatures.

Mathematical analysis of the components of error in the measurements of ionic electric conductance has shown that the most important one is that component, which is due to the electrolysis phenomenon. Its value is proportional to the amount of electricity ($Q = I.t$, wherein Q is the amount of electricity; I-is curent intensity; $t$ is time of the current flow) which passes through the object during the measurement period.

Therefore, the error may be reduced by lowering the current and by reducing the time of its passage.

The lowering of current resuls in more stringent requirements to the sensitivity of the apparatus used to determine the elctric conductance. This would result in more sophisticated measuring equipment, which is contrary to the operation requirements. The reduction of time of current passage through the object appears more expedient. In this case the misleading factors (electrolysis, heating of the object and like) will have no time to substantially distort the measurement results.

The errors due to polarization of contacts of the measuring electrode will not be reduced in this case, since the time of the growth of polarization EMF is too short (of the order of 20 milliseconds). However, an appropriate selection of the material of the electrode contacts having stable electrochemical and mechanical characteristics (such as platinum) will permit to keep this error almost constant, which can be taken into account during the calibration of the apparatus.

Our calculations and research have shown that the error in measuring the electric conductance is directly proportional to the time of the passage of current through the object during the measurement.

Therefore, from the viewpoint of increasing the accuracy it is desirable to pass current through the object during a very short time interval. Minimum duration of the current pulse, is however, limited by the possibility of designing a simple apparatus for recording and evaluation of the measurement results. With the pulse method of measurement (which is herein contemplated) it is not possible to indicate the value of a short-term current pulse proportional to the electric conductance of the object by means of a pointer meter (such as an ammeter) due to the inertia of the latter. Therefore, there is a need in the use of memory means in the indicator circuit. The simplest solution of the problem is the use of a charging ("memory") capacitor which, after being charged up to a voltage proportional to the electric conductance to be determined, will "memorize" this value after the disappearance of the current pulse during the time sufficient for reading the measurement result. In order to prevent the memory capacitor from discharging through the charging source, a diode is to be inserted in the charging circuit.

Since the process of the measurement proper (current passage through the object) proceeds rapidly, manual manipulations during the measurement are impossible, and the pulse method of measurement cannot be applied with the use of a balance bridge circuit.

Referring to FIG. 1, there is shown the first embodiment of a functional diagram of the apparatus for measuring ionic electric conductance.

A single-pulse generator 1 is coupled to a circuit consisting of electrodes 2 connected in series, which are to be immersed into a tested object 3, and a resistor 4. A diode 5 is adapted to charge a memory capacitor 6 and to prevent it from being discharged after the test pulse has disappeared. A switch 7 discharges the capacitor 6 in the position $a$ prior to the measurement, while in the position $b$ it will start the generator 1 during the measurement.

The circuit functions as follows.

After the switch 7 has been put into the position $b$, the generator 1 sends a short pulse to the circuit consisting of the object resistance and the resistor 4. A voltage pulse $U_x$ is formed at the resistor 4, the amplitude of this pulse being proportional to the current pulse in the circuit, and hence to the electric conductance to be determined. The pulse $U_x$ will charge via the diode 5 the memory capacitor 6 up to the voltage $U_x$, which will be maintained across the capacitor 6 after the current pulse has disappeared. The voltage $U_x$ will be maintained across the capacitor 6 for a long time (since the back resistance of the diode 5 is high) sufficient for measuring the voltage across the capacitor 6. Upon putting the switch 7 into the position $a$ the capacitor 6 will be discharged, and the circuit will return into its initial position.

In order to measure the voltage across the capacitor 6 (and therefore, the electric conductance), a DC high-input resistance voltmeter (such as a cathode voltmeter) would be required to prevent the capacitor 6 from discharging therethrough. However, it is difficult to build such an instrument using transistors, since transistorized circuits exhibit considerable temperature and time drift. The use of DC amplifier of the voltmeter according to the modem system results in considerable complication of the apparatus which must be of a small, size and simple in design.

Figure 2:
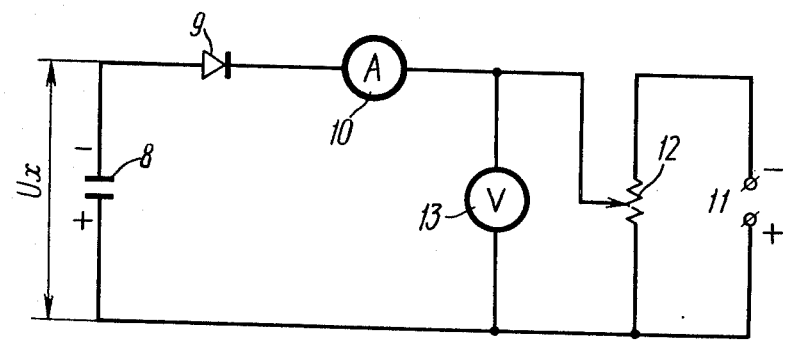
FIG. 2 shows a comparison circuit for measuring voltage in the apparatus according to the invention.

The problem was solved by using a comparison circuit for measuring voltage across the capacitor 6. The circuit may be similar to that shown in FIG. 2.

A memory capacitor 8 (FIG. 2) is coupled via a diode 9 and a microammeter 10 to DC power supply source 11 via a potentiometer 12. A pointer voltmeter 13 measures a voltage across the slider of the potentiometer 12 and the positive terminal of the power supply source 11.

There is a voltage $U_x$ across the capacitor 8 which is to measured.

Initially the slider of the poentiometer 12 is in the lowermost position. The coupling of the circuit 2, 3, 6, 5, 4, (FIG. 1) will not change the voltage $U_x$ across the capacitor 8 (FIG. 2), since the diode 9 is blocked. In order to measure $U_x$ (and hence the electric conductance to be determined), it is necessary to turn slowly the knob of the potentiomenter 12 while observing the readings of the microammeter 10. Upon the appearance of current the turning of the knob of the potentiometner 12 is stopped. The appearance of current indicates that the potentials at the components 8 and 12 are equal.

Therefore, the reading of the, voltmeter 13 will (on a predetermined scale) correspond to the electric conductance being measured.

The error of the measurement, as it was mentioned hereinabove, depends upon the duration of current pulse, too short duration resulting, however, in more complicated memory means and indicator circuit.

The following condition must be fulfilled for operation of the circuit; the capacitor 8 should have the time for complete discharge during the passge of current. Therefore, the value of the capacitor should be sufficiently low. But in this case the capacitor 8 will be rapidly discharged upon the appearance of current, thereby distorting the result of the measurement. The experiments have shown that the following values are optimal for the above-described circuit;

| | |
|---|---|
| $\tau$ - duration of pulse | — 0.25 sec; |
| C - memory capacitor (electrolytic capacitor) | — 300 $\mu$f; |
| Q - amount of electricity passing through the object | — 1.35·10$^{-3}$C; |
| $\Delta$ % - error of measurement | — ±2.5%. |

With continuous current flow through the object the error was in the range of 7 - 8%.

Taking into account the above consideration, there has been built an apparatus using the principles of the pulse method of measurement, which is applicable for the purposes of the diagnosis of the physiological state of the sexual sphere in cows.

The tests of the apparatus with other objects containing an electrolytic phase (milk, blood, tissues, gastric juice, sperm, salt solutions and the like) have shown that in all cases the errors of measurement did not exceed ±2.5%.

In addition, the pulse method offers the advantage consisting in that it may be used in the cases, where continuous current flow results in changes of the physiological parameters of the object (neurons, muscles and fibers). Power supply is provided by two dry galvanic cell batteries. The apparatus circuit comprises stabilizing components so as to ensure its normal function with fluctuations of the power supply voltage from 8 to 9 within the ambient temperature range from +5° C to +35° C (at a relative air humidity up to 80%).

Figure 3:
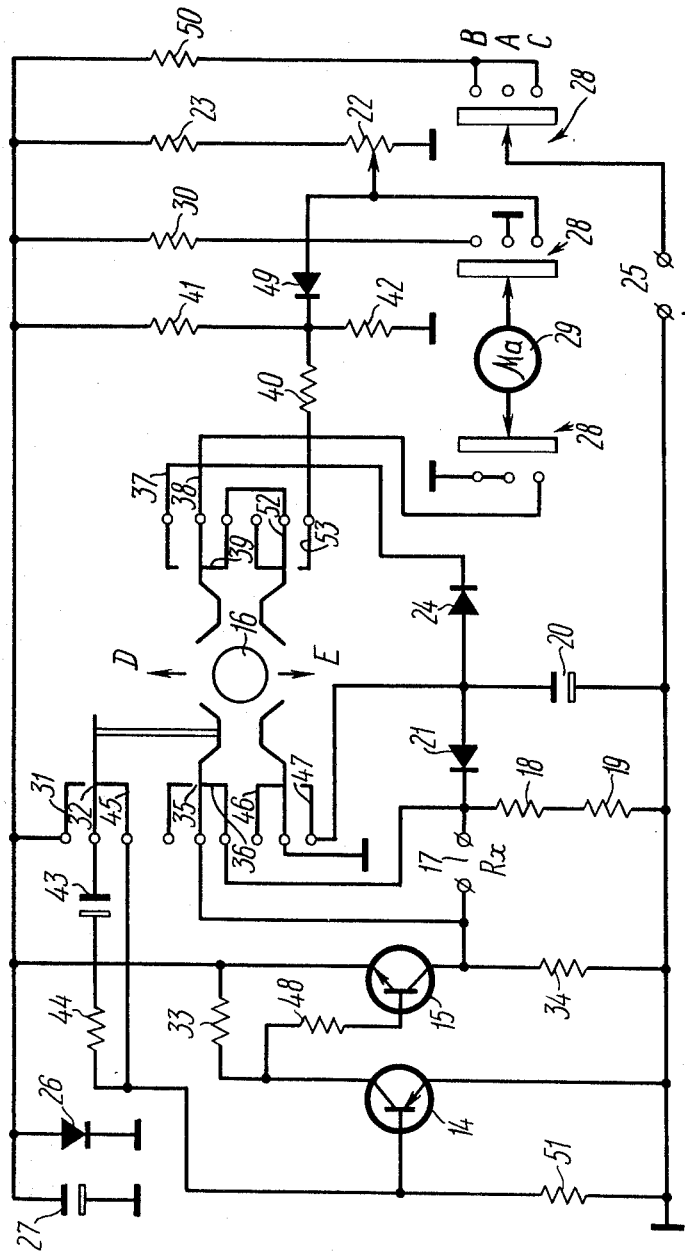
FIG. 3 is a principal wiring diagram of the apparatus according to the invention for measuring ionic electric conductance of biological objects.

The principle wiring diagram of the apparatus is shown in FIG. 3.

The apparatus comprises the following units and stages:

A single square-pulse generator including transistors 14 and 15 (FIG. 3); a control switch 16; a measuring circuit-measuring electrode (sensor) circuit-terminals 4, 17 and resistors 18 and 19 (the resistor 19 is adapted to select a required resistance value in the charging circuit of a capacitor 20); memory means — a capacitor 20 and a diode 21; reading circuit — a potentiometer 22, 23 and a diode 24; a power supply unit — a battery 25, a Zener diode 13 and a capacitor 27; a function selector 28 of an indicator 29. The circuit functions as follows.

Initial Position of the Controls

The selector 28 is in the position A (Off).
The switch 16 is in the neutral position.

Preparation of the Apparatus for Operation

The selector 28 is put into the position B "check". After checking the power supply, the selector 28 is put into the position C (measurement). Power is supplied to the circuit. The transistor 14 is blocked since the potentials at its base and emitter are zero (contacts 31 and 32 of the switch 16 are open). Current does not flow through the transistor 14, and a voltage drop across a resistor 33 is zero. Therefore, the transistor 15 is also blocked, since the potentials of its base and emitter are equal. With the transistor 15 being blocked, current is not flowing therethrough, and a voltge drop across a resistor 34 (pulse generator output) will be equal to zero. The sensor terminals are short-circuited by contacts 35, 36, and the indicator circuit (the microammeter 29) is open (contacts 27, 38) by the switch 16. Voltage across the "memory" capacitor 20 is zero. L Measurement of Electric Conductance The measuring electrode (sensor) is coupled to the terminals 17, treted with an alcohol-impregnated pad and introduced into the object being tested. The switch 16 is put into the position D (pulse).

A capacitor 43 begins to change. The charging circuit comprises: the negative terminal of the power supply, a resistor 44, as well as a resistor 51 and the resistance of the base-emitter junction of the transistor 14 connected in parallel. The charge current creates at the base-emitter junction a voltage drop "U" making the transistor 14 conductive. Negative potential at the collector of the transistor 14 is decreased to make the transistor 15 conductive. The current flowing through the transistor 15 results in a voltage drop across the resistor 34, which is about equal to the power supply voltage ($U_{out}$). $U_{out}$ will be maintained until the capacitor 43 is charged. At the end of the charging of the capacitor 43 the current passing through the transistor will become as low as the voltage drop at the base-emitter junction of the transistor 14 will become lower than the voltage corresponding to the beginning of conductivity of the transistor.

The transistor 14 will be blocked, thereby blocking the transistor 15. Accordingly, the voltage drop $U_{out}$ across the resistor 34 will also disappear. Thus, upon putting the switch 16 into the position D, a negative voltage pulse $U_{out}$ is formed across the resistor 34, the duration of the pulse being determined by the parameters of the charging circuit of the capacitor 43.

The negaive pulse $U_{out}$ is fed to the measuring circuit consisting of the resistance being measured and the resistors 18,19. The amplitude of the pulse at the resistors 18, 19 will be proportional to the value of electric conductance being measured.

The pulse $U_x$ will charge the capacitor 20 via the diode 21, and the voltage will be maintained thereacross upon the disappearance of the test pulse $U_{out}$, due to the high back resistance of the silicon diodes 21 and 24 (more than $500.10^6$ ohm).

Therefore, after the first manipulation with the switch 16 a voltage proportional to the value being measured will appear across the capacitor 20, and this voltage will be maintained for a long time (the discharge time constant of the capacitor 20 is of about $15.10^3$ sec).

Direct measurement of the voltage across the capacitor 20 by means of a pointer indicator is not possible due to low resistance thereof which would at once discharge the capacitor 20. For this reason the above-said voltage is measured in the apparatus by an indirect method (by the comparison method). For that purpose the knob of the potentiometer 22 should be slowly turned to the right, while observing the indicator to reveal the appearance of current. In so doing, negative potential will grow at the negative pole of the diode 24 (via the slider 22, indicator 29 and contacts 37, 38 of the switch 16). The moment of the appearance of current will indicate that the potential at the capacitor 20 and that at the negative electrode of the diode 24 are equal, and the diode is partially open. At that moment the rotation of the knob of the potentiometer 22 should be stopped. In this position the voltage across the slider 22 will correspond to the value $U_x$. In order to read that voltage, the switch 16 is put into the position E "Reading". Thus, the positive terminal of the microammeter 29 is coupled via contacts 52, 53, 38, 39 of the switch 16 and an additional resistor 40 to that point of the circuit, whereto an initial bias was applied via resistors 41, 42. This bias is necessary to place the microammeter scale into a required range of the electric conductance values ($H_x$). The negative terminal of the indicator will be coupled to the slider of the potentiometer 22. In this case the deflection of the indicator pointer is proportional to the voltage $U_x$ at the slider 22, and hence to the value $H_x$ being measured. In addition, upon putting the switch 16 into the position E the capacitor 43 is discharged via the resistor 44 and the contacts 32 and 45 of the switch 16, the contacts 35 and 36 will short-circuit the measuring electrode to remove therefrom the potential, which has appeared as a result of electrochemical processes takin place at its contacts. Thus, the capacitor 20 is discharged via the contacts 46, 47 of the switch 16, A resistor 48 is adapted to limit the base current of the transistor 15.

After the switch 16 has been put into the neutral position, the circuit is returned to the initial state.

A diode 49 prevents the pointer of the microammeter from being deflected to the left at the opposite polarity voltage which may appear thereacross during some intermediate manipulations.

A resistor 50, the Zener diode 26 and the capacitor 27 constitute stabilization and matching circuits of the circuit components as to the power supply.

The apparatus is built as a portable device. The sensor is placed inside the apparatus.

All the components of the apparatus and a printed circuit board are mounted on the upper panel, where all controls and switching members are also arranged.

The size of the sensor and its design provide for measurement of the electric conductance in small volumes (0.2 ml).

What is claimed is:

1. A method of measuring ionic electric conductance of biological objects by establishing electric current flow in a predetermined zone of the object being tested, particularly measuring the electrical conductance of the cervical secretion of cows for the purpose pf pregnancy diagnosis, comprising the step of passing in the course of measurement through a predetermined zone of the object being tested such a current and during such a relatively short time interval that the total amount of electricity passing through the object being tested during the measurement period should not exceed about $1.35 \cdot 10^{-3}$C with a corresponding permissible error of the measurement being of ±2.5%, wherein electric current is passed through sampled secretion in the course of the measurement for a time not exceeding 0.25 sec.

2. A method as claimed in claim 1, wherein the process of passing current through the object being tested and the process of evaluating the current, which has been passed through, are time-shared by first passing through the object a current during a short time interval and then measuring the value of the current, which has been passed through, and evaluating it.

3. The method as claimed in claim 1, performed by an apparatus comprising: a power supply source; measuring electrodes coupled thereto, which are adapted to be positioned adjacent said zone of the object being tested; a current value indicator; means for application of a short-term current pulse to said electrodes, and means for memorizing the current, which has passed through the object, said current being proportional to the value of electric conductance of the object.

4. A method as claimed in claim 3, whrein the apparatus is provided with means for short-circuiting the measuring electrodes on completion of the measuring step, whereby the electrochemical potentials are removed from the electrodes surface.

5. A method as claimed in claim 3, wherein means for application of a short-term current pulse to the electrodes of the apparatus comprises a current pulse relaxation generator.

* * * * *